United States Patent [19]

Johnston et al.

[11] Patent Number: 5,505,947
[45] Date of Patent: Apr. 9, 1996

[54] ATTENUATING MUTATIONS IN VENEZUELAN EQUINE ENCEPHALITIS VIRUS

[75] Inventors: Robert E. Johnston; Nancy L. Davis, both of Chapel Hill, N.C.; Jonathan F. Smith, Sabillasville; Franziska B. Grieder, Bethesda, both of Md.

[73] Assignee: The University of North Carolina at Chapel Hill, Chapel Hill, N.C.

[21] Appl. No.: 250,445

[22] Filed: May 27, 1994

[51] Int. Cl.$^6$ .................. A61K 39/193; C12N 7/00; C12N 7/04; C12N 15/40
[52] U.S. Cl. .................. 424/218.1; 435/235.1; 435/236; 536/23.72; 424/199.1
[58] Field of Search .................. 536/23.72; 435/235.1, 435/236, 172.3; 424/218.1, 199.1; 935/12, 65

[56] References Cited

U.S. PATENT DOCUMENTS 5,185,440  2/1993  Davis et al. .................. 536/23.72

FOREIGN PATENT DOCUMENTS

WO92/10578  6/1992  WIPO .

OTHER PUBLICATIONS

Davis, N. L. et al. 1993. J. 611. Biochem. Suppl. 17D, p. 79.
Davis, N. L. et al. 1990. Vaccines 90 pp. 109–113.
Frolov, I. V. et al. 1991, Doklady Biochem. vol. 318 pp. 144–146.
Frolov, I. V. et al. 1992. Doklady Biol. Sci. vol. 326 pp. 466–469.
Glasgow, G. M. et al. 1994. J. Gen. Virol. vol. 75 pp. 663–668.
Polo, J. M. et al. 1990. J. Virol. vol. 64 pp. 4438–4444.
Heidner, H. W. et al. 1994. J. Virol. vol. 68 pp. 2683–2692.
Glasgow, G. M. et al. 1991. Virol. vol. 185 pp. 741–748.
Vrati, S. et al. 1986, Virol. vol. 151 pp. 222–232.
Engler, R. J. M. et al. 1992. J. Med. Virol. vol. 38 pp. 305–310.
Kinney, R. M. et al. 1989. Virol. vol. 170 pp. 19–30.
Davis, N. L., A Molecular Genetic Approach to the Study of Venezuelan Equine Encephalitis Virus Pathogenesis, *Arch Virol* 9:99 (1994).
Davis, N. L., Attenuating Mutations in the E2 Glycoprotein Gene of Venezuelan Equine Encephalitis Virus: Construction of Single and Multiple Mutants in a Full–Length cDNA Clone, *Virology* 183:20 (1991).
Frolov, I. V., et al., Recombinant VEE Virus Expresses HBsAg, Proceedings, IXth International Congress of Virology, p. 67. (Aug. 8–13, 1993).
Hahn, C. S., et al, Infectious Sindbis Virus Transient Expression Vectors for Studying Antigen Processing and Presentation, *Proc. Natl. Acad. Sci.*, 89:2679 (1992).

*Primary Examiner*—Mary E. Mosher
*Attorney, Agent, or Firm*—Bell, Seltzer, Park & Gibson

[57] ABSTRACT

Novel attenuating mutations of Venezuelan Equine Encephalitis (VEE) are disclosed. Further aspects of the invention include an infectious VEE virus transcript encoded by cDNA clones, infectious VEE virus particles, and pharmaceutical formulations containing such infectious particles. Also disclosed are recombinant VEE virus containing a heterologous RNA segment.

11 Claims, 6 Drawing Sheets

5,505,947

1

ATTENUATING MUTATIONS IN VENEZUELAN EQUINE ENCEPHALITIS VIRUS

FIELD OF THE INVENTION

The present invention relates to live attenuated vaccines in general, and particularly relates to attenuated vaccine produced from Venezuelan Equine Encephalitis (VEE) virus.

BACKGROUND OF THE INVENTION

Live, attenuated viral vaccines are among the most successful means of controlling viral disease. However, for some virus pathogens, immunization with a live virus strain may be either impractical or unsafe. One alternative strategy is the insertion of genes encoding immunizing antigens of such agents into the vaccine strain of another virus. However, relatively few such systems are currently available.

Hahn et al., *Proc. Natl. Acad. Sci. USA* 89, 2679 (1992), describes Sindbis virus constructs which express a truncated form of the influenza hemagglutinin protein. The constructs are used to study antigen processing and presentation in vitro and in mice. Although no infectious challenge dose is tested, it is also suggested that such constructs might be used to produce protective B- and T-cell mediated immunity. The final paragraph of the discussion section states: "Although SIN is not likely to be approved for use as a human vaccine, a parallel approach to the one used here for SIN may be applicable for developing live-attenuated vaccine strains using viruses with similar replication strategies, such as attenuated strains of Venezuelan equine encephalitis virus . . . . (citing Davis et al.)" Insofar as applicant is aware, a problem with the Sindbis vector is that the heterologous insert is unstable therein and is "kicked out" of the vector, with the practical limit for stable inserts being about 1 kb.

Davis et al., U.S. Pat. No. 5,185,440, describes cDNAs encoding the VEE virus and attenuated mutations which may be incorporated therein for use in making a vaccine. The use of a subgenomic expression system is neither suggested nor disclosed.

SUMMARY OF THE INVENTION

A first aspect of the present invention is a method of protecting a subject against a disease. The method comprises administering a recombinant Venezuelan Equine Encephalitis (VEE) virus to the subject in an effective immunogenic amount, with the VEE virus containing at least one attenuating mutation (and typically two or even three different attenuating mutations), and with the VEE virus containing a heterologous RNA segment. The heterologous RNA segment comprises a promoter operable in the subject operatively associated with a RNA encoding an immunogenic protein or peptide effective for protecting the subject from the disease. The heterologous insert may, optionally, itself serve as an attenuating mutation.

In one preferred embodiment, the heterologous RNA segment of the VEE virus is derived from the genome of a pathogenic organism. According to this embodiment, the heterologous RNA segment comprising the promoter operatively associated with the RNA encoding the immunogenic protein or peptide is effective for protecting the subject from the disease caused by the pathogenic organism.

2

A second aspect of the present invention is a DNA comprising a cDNA clone coding for an infectious Venezuelan Equine Encephalitis (VEE) virus RNA transcript and a heterologous promoter positioned upstream from the cDNA clone and operatively associated therewith, and further comprising at least one attenuating mutation selected from the group consisting of codons at E1 amino acid 272 which specify an attenuating mutation; codons at E1 amino acid 81 which specify an attenuating mutation; and codons at E1 amino acid 253 which specify an attenuating mutation.

A third aspect of the present invention is a DNA comprising a cDNA clone coding for an infectious Venezuelan Equine Encephalitis (VEE) virus RNA transcript and a heterologous promoter positioned upstream from said cDNA clone and operatively associated therewith, and further comprising: (a) a first attenuating mutation which is a codon at E1 amino acid 253 which specifies an attenuating mutation; and (b) a second attenuating mutation which is an inactivated E3 amino acid 56 to 59 cleavage recognition site.

Further aspects of the present invention include an infectious VEE virus RNA transcript encoded by cDNA clones as given herein; infectious VEE virus particles containing such RNA transcripts; and pharmaceutical formulations comprising such infectious VEE virus particles, in an effective immunogenic amount, in a pharmaceutically acceptable carrier.

Frolov et al., *Proceedings IXth International Congress of Virology*, Glasgow, Scotland, Aug. 8–13, 1993, pg. 67, discusses recombinant VEE viruses which express a Hepatitis B virus antigenic protein. The use of an attenuated VEE virus, strain 230, is described. However, it is not suggested that the attenuated virus itself be administered to humans. To the contrary, these viruses are used to manufacture the antigenic Hepatitis B virus proteins themselves in tissue culture, which are then harvested and administered to humans. Strain 230 itself replicates poorly, if at all, in humans.

The foregoing and other objects and aspects of the present invention are explained in detail in the specification set forth below.

DETAILED DESCRIPTION OF THE INVENTION

Figure 1:
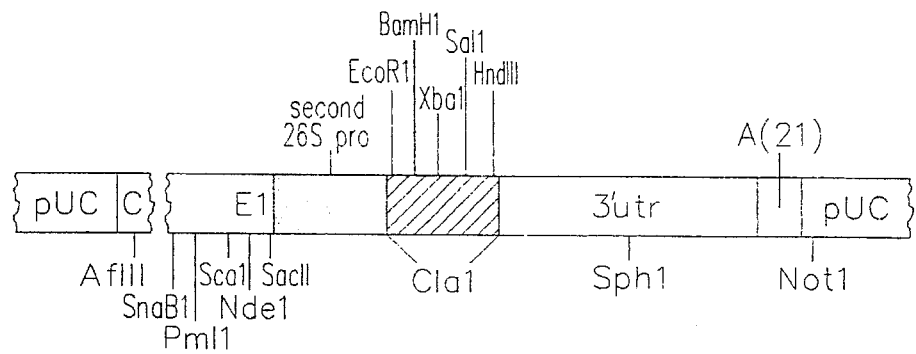
FIG. 1 is an illustration of the structure of the shuttle vector containing the structural genes of VEE with three attenuating mutations in the E2 gene, and a second 26S promoter and multiple cloning site inserted directly downstream from the C-terminus of E1, in the 3.2 kb pUC118 plasmid.

Complementary DNA sequences encoding live Venezuelan Equine Encephalitis (VEE) virus and pharmaceutical formulations containing the same are known. See, e.g., N. Davis et al., U.S. Pat. No. 5,185,440 (Applicant specifically intends that the disclosures of all patent references cited herein be incorporated herein by reference in their entirety).

The phrases "attenuating mutation" and "attenuating amino acid" as used herein mean a nucleotide mutation or an amino acid coded for in view of such mutation which result in a decreased probability of causing disease in its host (i.e., a loss of virulence), in accordance with standard terminology in the art (See, e.g., B. Davis et al., *Microbiology*, 132 (3d ed. 1980), whether the mutation be a substitution mutation or an in-frame deletion mutation. The phrase "attenuating mutation" excludes mutations which would be lethal to the virus. Examples of known VEE attenuating mutations include codons at E2 amino acid position 76 which specify an attenuating mutation, codons at E2 amino acid position 209 which specify an attenuating mutation, and codons at E2 amino acid 120 which specify an attenuating mutation (see, e.g., U.S. Pat. No. 5,185,440 to N. Davis et al.); a G to C mutation at viral RNA nucleotide 3.

Novel attenuating mutations disclosed herein which may be used to carry out the present invention include codons at E1 amino acid 272 which specify an attenuating mutation (preferably a substitution mutation, such as a threonine or serine (most preferably threonine)); codons at E1 amino acid 81 which specify an attenuating mutation (preferably a substitution mutation, such as an isoleucine or leucine (most preferably isoleucine)); and codons at E1 amino acid 253 which specify an attenuating mutation (preferably a substitution mutation such as a serine or threonine (most preferably serine)).

A novel pair of attenuating mutations which may be inserted together in a cDNA clone encoding an attenuated VEE virus is (a) a first attenuating mutation which is a codon at E1 amino acid 253 which specifies an attenuating mutation; and (b) a second mutation which is an inactivated E3 amino acid 56 to 59 cleavage recognition site. An advantage of this combination of attenuating mutations is that the inactivated cleavage site, of itself, is lethal to the virus. Thus, if the attenuating mutation at E1 amino acid 253 reverts to the virulent wild-type, the remaining mutation kills the virus. The E3 amino acid 56 to 59 cleavage recognition site may be inactivated by any suitable means: the cleavage recognition site may be deleted, in whole or in part; a substitution mutation may be made therein (e.g., an arginine to aspartic acid substitution mutation at amino acid 59).

Attenuating mutations may be introduced into cDNAs encoding live VEE by any suitable means, such as site-directed mutagenesis (see, e.g., U.S. Pat. No. 4,873,192 to Kunkel).

The immunogenic protein or peptide, or "immunogen" may be any immunogen suitable for protecting the subject against a disease, including but not limited to microbial, bacterial, protozoal, parasitic, and viral diseases. For example, the immunogen may be an influenza virus immunogen (e.g., an influenza virus hemagglutinin (HA) surface protein, or an equine influenza virus immunogen), or a lentivirus immunogen (e.g., an equine infectious anemia virus immunogen, a Human Immunodeficiency Virus (HIV) immunogen, such as an HIV-1 immunogen, or an HIV-2 immunogen). The immunogen may also be a coronavirus immunogen (e.g., a transmissible gastroenteritis virus immunogen for pigs, or an infectious bronchitis virus immunogen for chickens,) or a flavivirus immunogen (e.g., a yellow fever virus immunogen or a Japanese encephalitis virus immunogen). If desired, an advantage of the instant invention is that the heterologous insert containing the DNA encoding the immunogen as given above may be a relatively large insert, at least 1 kilobase in length.

The heterologous promoter is preferably a Venezuelan equine encephalitis virus 26S subgenomic promoter. This definition is intended to include derivatives of this promoter such as deletion mutants thereof, so long as activity as a promoter is retained.

Subjects which may be administered the live attenuated viruses and vaccine formulations disclosed herein include both human and animal (e.g., horse, donkey, pigs, mouse, hamster, monkey, chicken) subjects.

Vaccine formulations of the present invention comprise an immunogenic amount of a live attenuated virus as disclosed herein in combination with a pharmaceutically acceptable carrier. An "immunogenic amount" is an amount of the attenuated virus sufficient to evoke an immune response, particularly an immune response to the protein or peptide encoded by the heterologous RNA carried by the virus, in the subject to which the virus is administered. An amount of from about $10^1$ to $10^5$ plaque forming units of the live virus per dose is suitable, depending upon the age and species of the subject being treated. Exemplary pharmaceutically acceptable carriers include, but are not limited to, sterile pyrogen-free water and sterile pyrogen-free physiological saline solution.

Administration of the live attenuated viruses disclosed herein may be carried out by any suitable means, including both parenteral injection (such as intraperitoneal, subcutaneous, or intramuscular injection), by in ovo injection in birds, and by topical application of the virus (typically carried in the pharmaceutical formulation) to an airway surface. Topical application of the virus to an airway surface can be carried out by intranasal administration (e.g., by use of a dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. See, e.g., U.S. Pat. No. 5,304,125 to D. Leith; U.S. Pat. No. 5,299,566 to C. Davis and R. Snyder; U.S. Pat. No. 5,290,550 to R. Fisher and W. Metzger; and U.S. Pat. No. 5,292,498 to R. Boucher.

The following examples are provided to illustrate the present invention, and should not be construed as limiting thereof.

EXAMPLE 1

Construction of a "Second Promoter" Expression Vector

A full-length cDNA clone derived from the TRD strain of VEE, pV3507, and containing three attenuating mutations in the E2 gene was employed in this study. The mutations occur at E2 76 lys, E2 120 lys and E2 209 lys, as reported in Davis et al., *Virology* 183:20 (1991). The cDNA clone was digested with Tth111I, converted to blunt ends with Klenow fragment of *E. coli* DNA polymerase, and then digested with EcoRI. The 3.9 kb fragment was isolated and ligated with M12 mp19 RF DNA that had been digested with HindIII, treated with Klenow fragment and then digested with EcoRI. The resulting M13 phage, TE3, contained the structural gene region of pV3507, but not the 26S promoter region. The HindIII site was regenerated in the ligation. Single-stranded DNA from phage was produced following transformation of *E. coli* CJ236 (dut-ung-) with TE3 and used in the procedure outlined by Kunkel, *Proc. Natl. Acad. Sci.* USA 82:488 (1985), with a synthetic oligonucleotide designed to give the following insertion (in bold):

3' end of E1 gene - −34/+14 26S promoter-ClaI site - the 5' end of 3' untranslated region
nt11,315–nt11,326                           nt11,327–nt11,338

AAACATAATTGA/GAGGGGCCCCTATAACTCTCTACGGCTAACCTGAATGGACTACGACATCG/ATACAGCAGCAA (SEQ ID NO: 1)

The regions flanking the inserted sequence are identified by nucleotide numbers based on the full-length VEE sequence, as identified by Kinney et al., *Virol.* 170:19 (1989).

The correct insertion was identified initially by screening with ClaI digestion of phage RF DNA, and confirmed by sequencing across the junction between the E1 gene and the 3'-untranslated region on single-stranded phage DNA.

Thereafter, the DNA fragment containing the pV3507 structural genes and the inserted second 26S promoter was subcloned into pUC118 using HindIII and EcoRI. The HindIII and EcoRI sites were removed by digestion followed by conversion to blunt ends with Klenow fragment and religation to form the pUC118 second promoter clone.

A 1.5 kb SalI-SalI "stuffer" fragment lacking an initiator AUG codon was isolated from the glycoprotein gene region of the TR5000 full-length Sindbis clone (identified by Schoepp et al., *Virology* 193:149 (1993)), and inserted into the SalI site of the ClaI2 adaptor plasmid. The ClaI2 plasmid containing a multiple cloning site (mcs) flanked by ClaI sites was identified by Hughes et al., *J. Virol.* 61:3004 (1987).

Using ClaI, the multiple cloning site containing the inserted TR5000 sequence was cloned into the unique ClaI site of the pUC118 second promoter clone. Digestion with SalI and self-ligation produced the shuttle vector with the structure shown in FIG. 1.

Figure 2A:
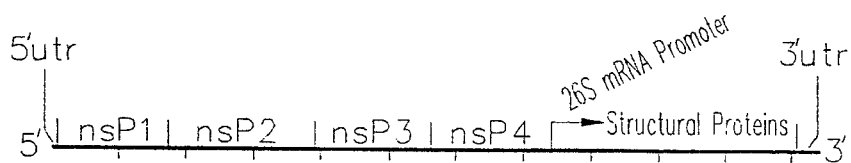
FIGS. 2a–2c illustrate double promoter vectors.
Figure 2B:
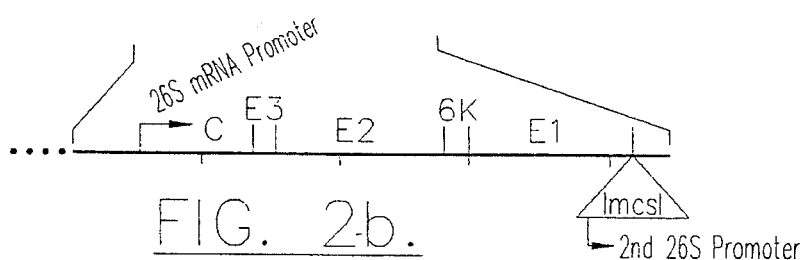
Figure 2C:
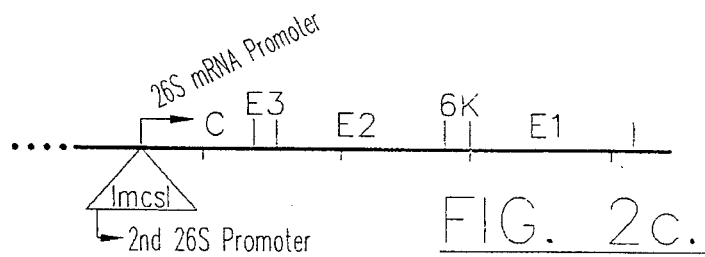

Thereafter, a viable full-length VEE second promoter expression vector including three attenuating mutations was prepared. The 3.4 kb AflII-NotI fragment isolated from the shuttle vector and containing a portion of the viral structural genes, the inserted downstream second promoter and the 3'-untranslated region, was used to replace the homologous AflII-NotI region of the pV3507 full-length clone. Transformants were screened with ClaI. Plasmids containing a ClaI site were linearized at the unique NotI site and transcribed in vitro with T7 RNA polymerase. Transcripts were quantitated by incorporation of alpha-$^{32}$P-labeled UTP. Thereafter, monolayers were transfected with transcripts using cationic liposomes (Lipofectin, BRL) and then overlaid with agarose for assay of plaque formation. The transcripts had specific infectivities comparable to those produced from the virulent pV3000 parent clone, indicating that they were fully infectious. FIGS. 2a–2c illustrate double promoter vectors. FIG. 2b is an illustration of pV4002, one of the downstream second promoter expression vectors.

EXAMPLE 2

Construction of an Expression Vector Containing the Influenza HA gene

The complete coding sequence of the HA gene from influenza strain PR/8 cloned into the BamHI site of pGem4 was obtained from Dr. Andy Caton at the Wistar Institute. The 1.7 kb BamHI fragment containing the HA sequence was ligated to BamHI digested, dephosphorylated shuttle vector DNA. V4002 DNA was cut with ClaI and dephosphorylated. Thereafter, the ClaI fragment containing the HA sequence was purified from the shuttle vector and ligated to prepare V4002 DNA. Clones containing the HA gene in the multiple cloning site downstream of the second 26S promoter were identified using digestion with HpaI. Clones including both coding (pV4002HA) and noncoding (pV4002AH) orientations were identified. Tests for the specific infectivity of the transcripts from these clones showed that they were as infectious as parental transcripts, but that these HA-containing genomes made smaller plaques on baby hamster kidney (BHK) cell monolayers. From these results, we determined that the VEE expression vector containing the three attenuating mutations in E2 and an inserted 1.7 kb HA gene was still replication competent, but appeared to grow more slowly than the vector without an insert.

EXAMPLE 3

Figure 3:
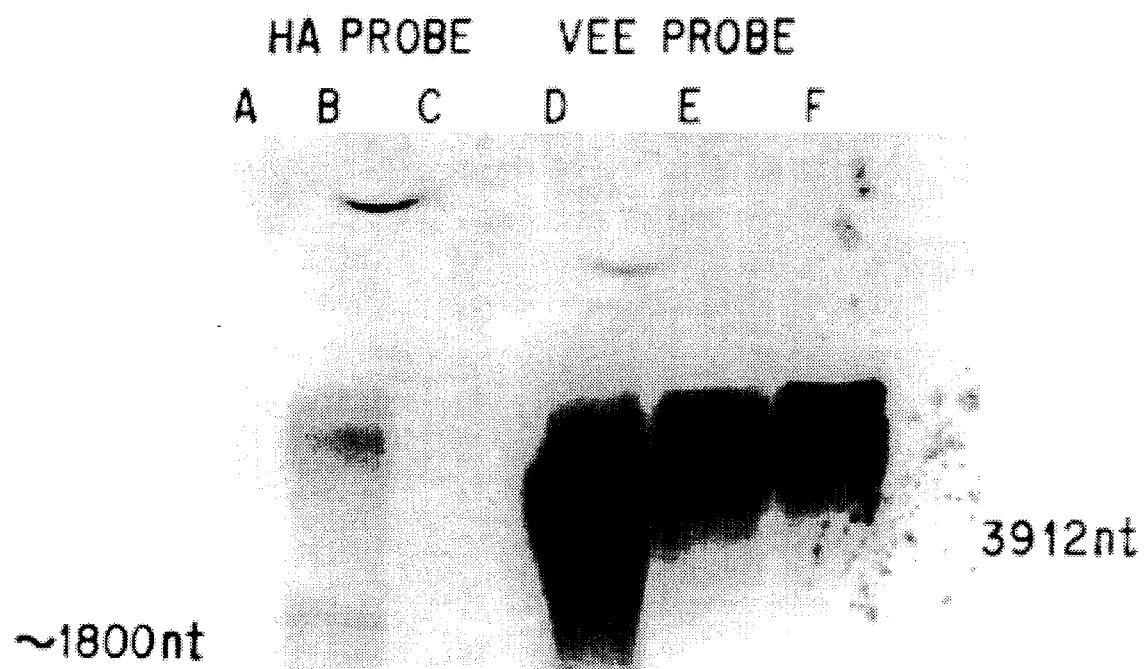
FIG. 3 is a Northern blot analysis of total intracellular RNA from baby hamster kidney (BHK) cells infected with an attenuated VEE mutant, with the mutant containing an HA gene inserted downstream of a second subgenomic promoter, or with the mutant containing an inserted HA gene in a non-coding orientation.

Stability Test of HA Containing Vectors During Replication in Tissue Culture Total RNA from vector-infected cells was analyzed for HA sequence-containing subgenomic RNA transcripts using Northern blots probed with VEE-specific or HA-specific probes as described in Sambrook et al., *Molecular Cloning* pp 7.39–7.52. Purified cytoplasmic RNA was glyoxylated, electrophoresed on agarose gels containing 0.01M sodium phosphate (pH 7), and transferred to Biotrans nylon membranes (ICN) with 7.5M sodium hydroxide. A VEE-specific $^{32}$P-labeled riboprobe was made using a subclone of the VEE glycoprotein gene region (nt 9493 to 10486) in the pGEM3 transcription vector, pGEM19. The pGEM4 HA clone obtained from Dr. Andy Caton at the Wistar Institute was used to generate an HA-specific $^{32}$P-labeled riboprobe. (The HA clone used contained a single nucleotide deletion which resulted in translation of a truncated protein. This mutation affected our ability to detect any expression of protein from this vector, although subgenomic HA-containing vital RNAs were detected.) Duplicate membranes were hybridized to either probe, dried and exposed to x-ray film. The results are illustrated in FIG. 3. Lanes A and D contain total cytoplasmic RNA from cells infected with a VEE strain containing three attenuating mutations in E2. Lanes B and E contain total cytoplasmic RNA from cells infected with the same mutant strain with a second subgenomic promoter followed by the influenza HA gene in the coding orientation (V4002HA). Lanes C and F contain total cytoplasmic RNA from cells infected with the VEE vector containing the HA gene in the noncoding orientation (V4002AH). Lanes A, B and C were probed with a $^{32}$P-labeled riboprobe complementary to a portion of the influenza HA gene. Lanes D, E and F were probed with a $^{32}$p-labeled riboprobe complementary to a portion of the VEE glycoprotein genes. The positions of ribosomal RNA markers were determined in a parallel lane stained with ethidium bromide. VEE genome length RNA (40S) was not detectable in this experiment.

The results indicate that deletion mutants of both the V4002HAand V4002AH vectors were arising during replication in tissue culture. However, some subgenomic RNAs in V4002HA-infected cells still contained HA sequences, and a significant fraction of these were of a size to accommodate the complete HA gene. The results revealed some instability of the inserted sequence.

EXAMPLE 4

Expression in Cultured BHK cells of Influenza PR/8 HA Gene from a Downstream Promoter Expression Vector with Two Attenuating Mutations The complete coding sequence of the HA gene from influenza PR/8 cloned into the HindIII site of pBR322 was obtained from Dr. P. Palese at the Mt. Sinai School of Medicine. The HA-containing HindIII fragment was ligated to the HindIII-cut and dephosphorylated shuttle vector (see FIG. 1). ClaI was then used to insert these HA sequences in both coding (V4036a) and noncoding (V4036e) orientations into a VEE second promoter expression vector that carried two attenuating mutations, E2 lys 209 and E1 thr 272. RNA transcribed in vitro from these clones showed comparable specific infectivities to RNA from the parental clone without the HA gene. Virus-containing supernatants obtained following transfection of BHK cells with cationic liposomes contained both small and large plaques, with the proportion of large plaques increasing with time. A greater proportion of large plaque variants were seen with V4036a, carrying HA in the coding orientation, than with V4036e.

Figure 4A:
FIGS. 4a–4d illustrate the immunocytochemical staining of VEE vector-infected BHK cell monolayers. Cells were infected with either influenza PR/8/34, VEE vector containing the complete influenza HA gene, VEE vector without insert.
Figure 4B:
Figure 4C:
Figure 4D:

BHK cell monolayers were infected at a multiplicity of 1 with either egg-grown influenza virus (PR/8 strain), the second promoter expression vector with the HA gene in the coding orientation, or the vector without the insert. At 6 hr post-infection, the monolayers were fixed with methanol:acetone (1:1) at − 20° C. and air dried. Using the horseradish peroxidase, biotin-avidin detection system (Vector labs), cells were tested for the presence of viral antigens using an HA-specific monoclonal antibody, or VEE-specific hyperimmune mouse ascites fluid, as primary antibodies. Cells were then counterstained with Meyer's hematoxylin. The monolayers infected with influenza PR/8 or with the coding HA vector showed positive staining for HA. The results are illustrated in FIGS. 4a–4d. FIG. 4a illustrates cells infected with influenza PR/8 stained with anti-HA antibody. FIG. 4b illustrates VEE HA-vector infected cells stained with anti-HA antibody. FIG. 4c illustrates cells infected with VEE vector without insert stained with anti-VEE antibody. FIG. 4d illustrates cells infected with VEE vector without insert stained with anti-HA antibody.

The HA stain in HA vector infected cells was cytoplasmic, and was as intense, under these conditions, as the staining for HA in the influenza-infected control monolayers. These results indicate that influenza HA can be expressed at normal levels from the second 26S promoter in a form that is detectable by this anti-HA monoclonal antibody, and that an infectious VEE virus carrying the inserted gene can be produced.

EXAMPLE 5

Protection of Mice Against Influenza Challenge

Figure 5A:
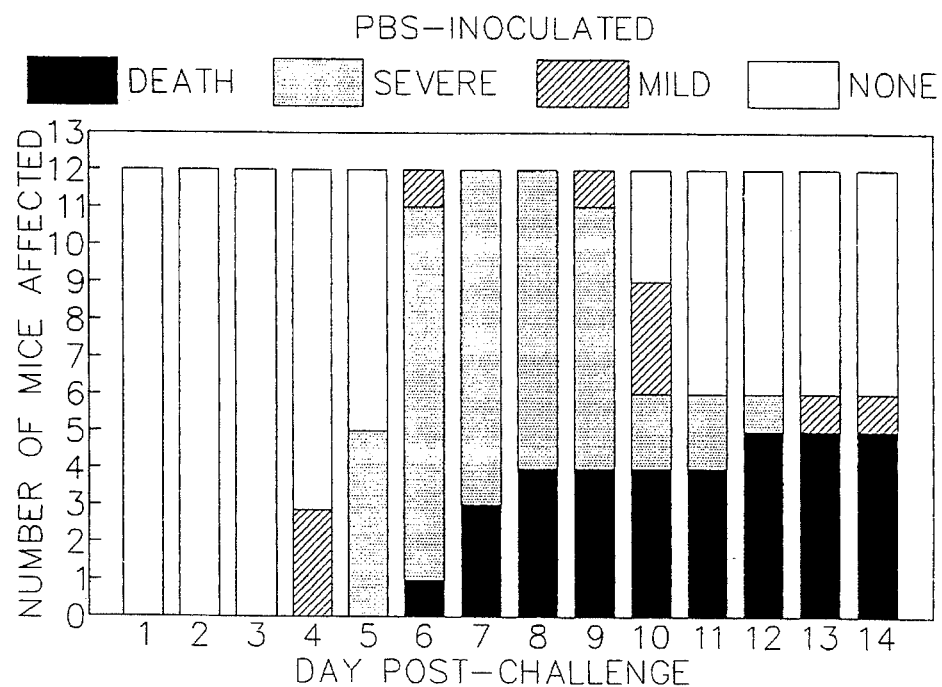
FIGS. 5a–5c are graphical illustrations of the clinical signs observed in inoculated mice challenged intranasally with influenza. Mice were inoculated with PBS, VEE vector without insert, or VEE vector with the complete influenza HA gene.
Figure 5B:
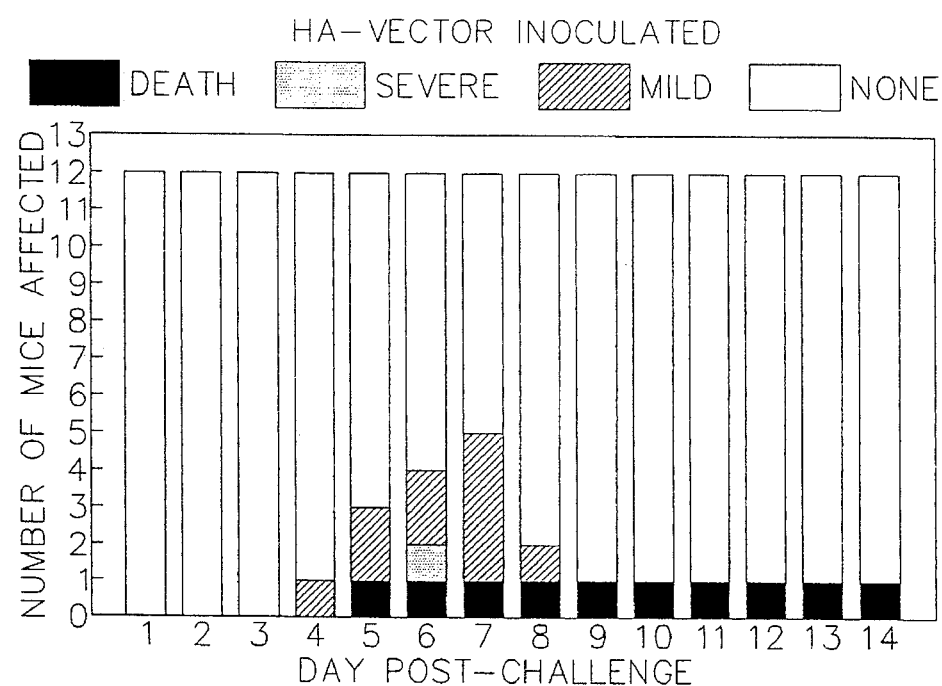
Figure 5C:
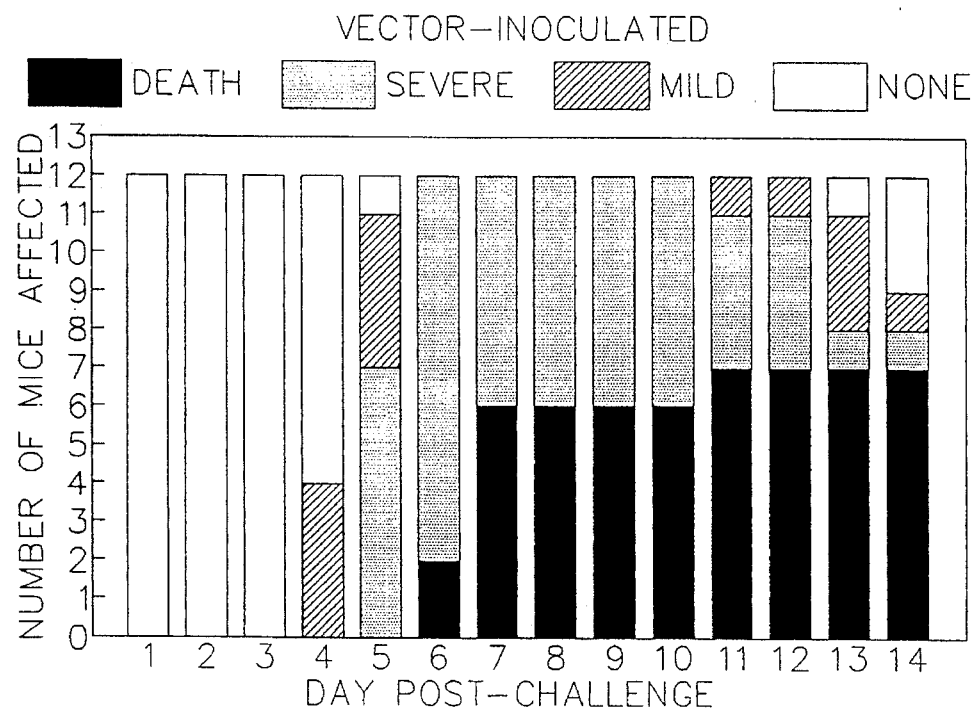

Four-week-old CD-1 mice were inoculated subcutaneously into each rear footpad with $1\times10^4$ pfu of (1) diluent (PBS) alone, (2) the HA-expressing doubly attenuated vector (V4036a), or with (3) the vaccine vector without insert. Three weeks later, the mice were challenged intranasally with $10^5$ EID$_{50}$ (50% egg infectious dose) of influenza virus. The results are reported in FIGS. 5a–5c. All 24 control mice suffered severe disease and 50% died. Only one of 12 HA-vector-inoculated mice died, and another exhibited signs of disease for one day and recovered.

Figure 6:
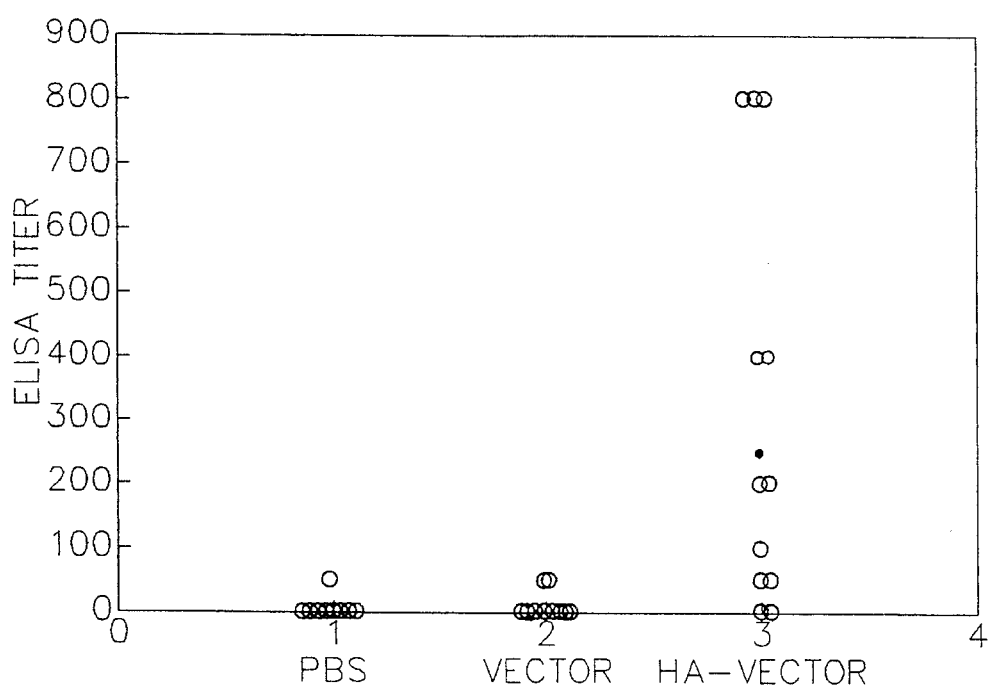
FIG. 6 is a graphical illustration of previral challenge anti-flu IgG ELISA titers of serum obtained from inoculated mice. Mice were inoculated with PBS, VEE vector without insert, or VEE vector with the complete influenza HA gene.

Pre-challenge anti-flu serum IgG ELISA titers were measured, and the results are illustrated in FIG. 6. The geometric mean ELISA titer of anti-HA serum IgG in the HA-vector inoculated mice was 246, while sera from only 3 of 24 control mice gave a detectable titer, and they were positive only at the lowest dilution tested (1:50). The two HA-vector-inoculated mice affected by the influenza challenge showed no detectable anti-HA IgG. Therefore, in 10 of 12 mice, the HA-vector elicited a detectable level of anti-HA serum IgG, and 11 of 12 mice were protected against lethal influenza challenge.

EXAMPLE 6

Protection of Mice Against Influenza Challenge

Figure 7:
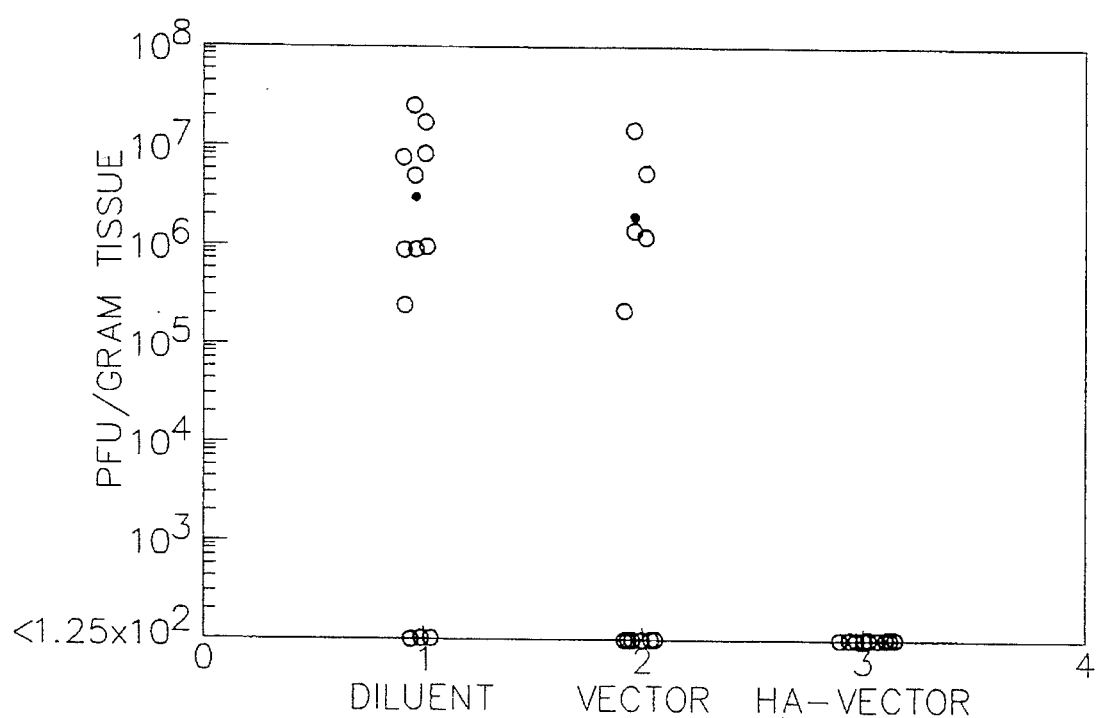
FIG. 7 is a graphical illustration of the titer of viable influenza virus observed in lung tissue of inoculated mice 4 days after challenge with influenza. Mice were inoculated with PBS, VEE vector without insert, or VEE vector with the complete influenza HA gene.

Four-week-old CD-1 mice were inoculated subcutaneously into each rear footpad with $1\times10^4$ pfu of (1) diluent (PBS) alone, (2) the HA-expressing doubly attenuated vector, or with (3) the vaccine vector without insert. Three weeks later, the mice were challenged intranasally with $10^5$ EID$_{50}$ (50% egg infectious dose) of influenza virus. The lungs were removed 4 days after challenge. Lung tissue was homogenized in PBS+0.1% BSA to give a 20% suspension, centrifuged, aliquoted and frozen at −70° C. For each animal, two aliquots were assayed for pfu on MDCK cells under agarose containing 0.1% trypsin. No influenza infectivity was detected in the lungs of mice previously immunized with the HA-vector at a detection level of $1.25\times10^2$ pfu/gm tissue (25 pfu/average lung). The geometric mean titers (represented by solid dots) calculated for the animals in the control groups with measurable virus titers, were $3.04\times10^6$ pfu/gm for PBS-inoculated mice, and $1.93\times10^6$ pfu/gm for mice inoculated with VEE vector alone. The results are reported in FIG. 7. The results suggest a very low level of challenge virus replication in the vaccinated animals.

The foregoing is illustrative of the present invention and is not to be construed as limiting thereof. The invention is defined by the following claims, with equivalents of the claims to be included therein.

That which is claimed is:

1. A DNA comprising a cDNA clone coding for an infectious Venezuelan Equine Encephalitis (VEE) virus RNA transcript and a heterologous promoter positioned upstream from said cDNA clone and operatively associated therewith, and further comprising at least one attenuating mutation selected from the group consisting of codons at E1 amino acid 272 which specify an attenuating mutation; and codons at E1 amino acid 253 which specify an attenuating mutation.

2. An infectious VEE virus RNA transcript encoded by a cDNA clone of claim 1.

3. Infectious VEE virus particles containing an RNA transcript of claim 2.

4. A pharmaceutical formulation comprising infectious VEE virus particles according to claim 3 in an effective immunogenic amount in a pharmaceutically acceptable carrier.

5. A DNA comprising a cDNA clone coding for an infectious Venezuelan Equine Encephalitis (VEE) virus RNA transcript and a heterologous promoter positioned upstream from said cDNA clone and operatively associated therewith, and further comprising:

a first attenuating mutation which is a codon at E1 amino acid 253 which specifies an attenuating mutation; and a second mutation which is an inactivated E3 amino acid 56 to 59 cleavage recognition site.

6. A DNA according to claim 5, wherein said E3 amino acid 56 to 59 cleavage recognition site is deleted.

7. A DNA according to claim 5, wherein said E3 amino acid 56 to 59 cleavage recognition site contains an inactivating substitution mutation.

8. A DNA according to claim 7, wherein said inactivating E3 amino acid 56 to 59 cleavage recognition site contains an arginine to aspartic acid substitution mutation at amino acid 59.

9. An infectious VEE virus RNA transcript encoded by a cDNA clone of claim 5.

10. Infectious VEE virus particles containing an RNA transcript of claim 9.

11. A pharmaceutical formulation comprising infectious VEE virus particles according to claim 10 in an effective immunogenic amount in a pharmaceutically acceptable carrier.

* * * * *

UNITED STATES PATENT AND TRADEMARK OFFICE
CERTIFICATE OF CORRECTION

PATENT NO. : 5,505,947
DATED : April 9, 1996
INVENTOR(S) : Robert E. Johnston et al.

It is certified that error appears in the above-identified patent and that said Letters Patent is hereby corrected as shown below:

Column 1, after Field of the Invention, please insert the following:

-- This invention was made with government funding under grant number DAMD17-91-C-1092 from the U.S. Army and grant number 5 R01 NS26681-05 from the National Institutes of Health. The Government has certain rights to this invention.--

Signed and Sealed this

First Day of September, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 74 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
AAACATAATT  GAGAGGGGCC  CCTATAACTC  TCTACGGCTA  ACCTGAATGG  ACTACGACAT        60

CGATACAGCA  GCAA                                                             74
```